United States Patent
Lombardo et al.

(10) Patent No.: US 11,540,542 B2
(45) Date of Patent: Jan. 3, 2023

(54) TASTE MODULATING ALDEHYDES

(71) Applicant: TAKASAGO INTERNATIONAL CORPORATION, Tokyo (JP)

(72) Inventors: Louis J. Lombardo, Washingtonville, NY (US); Michael E. Lankin, High Bridge, NJ (US); Maureen Blandino, North Bergen, NJ (US); Jennifer B. Tartaglia, Mahwah, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 53 days.

(21) Appl. No.: 16/331,880

(22) PCT Filed: Sep. 11, 2017

(86) PCT No.: PCT/US2017/051013
§ 371 (c)(1),
(2) Date: Mar. 8, 2019

(87) PCT Pub. No.: WO2018/049352
PCT Pub. Date: Mar. 15, 2018

(65) Prior Publication Data
US 2019/0208806 A1    Jul. 11, 2019

Related U.S. Application Data

(60) Provisional application No. 62/385,507, filed on Sep. 9, 2016.

(51) Int. Cl.
| | | |
|---|---|---|
| A23L 27/20 | (2016.01) | |
| A23G 4/06 | (2006.01) | |
| C07C 47/21 | (2006.01) | |
| A23L 27/00 | (2016.01) | |
| A23L 2/60 | (2006.01) | |
| A23L 27/30 | (2016.01) | |
| A23L 2/56 | (2006.01) | |
| A23L 27/12 | (2016.01) | |
| A21D 2/14 | (2006.01) | |
| A23C 9/13 | (2006.01) | |

(52) U.S. Cl.
CPC ............ *A23L 27/2024* (2016.08); *A21D 2/14* (2013.01); *A23C 9/1307* (2013.01); *A23G 4/06* (2013.01); *A23L 2/56* (2013.01); *A23L 2/60* (2013.01); *A23L 27/12* (2016.08); *A23L 27/30* (2016.08); *A23L 27/32* (2016.08); *A23L 27/36* (2016.08); *A23L 27/84* (2016.08); *A23L 27/86* (2016.08); *A23L 27/88* (2016.08); *C07C 47/21* (2013.01); *A23V 2002/00* (2013.01); *C07B 2200/09* (2013.01)

(58) Field of Classification Search
CPC ...... A23L 27/2024; A23L 27/88; A23L 27/32; A23L 27/86; A23L 27/30; A23L 27/12; A23L 27/84; A23L 27/36; A23L 2/56; A23L 2/60; A21D 2/14; A23C 9/1307; A23G 4/06; C07C 47/21; C07B 2200/09; A23V 2002/00

USPC ......................................... 426/548, 534, 650
See application file for complete search history.

(56) References Cited

U.S. PATENT DOCUMENTS

| | | |
|---|---|---|
| 3,920,752 A | 11/1975 | Lamparsky |
| 4,687,599 A | 8/1987 | Van Lier et al. |
| 6,287,620 B1 * | 9/2001 | Van Den Ouweland ............ A23L 27/75 426/534 |
| 10,035,972 B2 * | 7/2018 | Bedoukian ............ A61Q 19/002 |
| 2007/0014887 A1 | 1/2007 | Cherukuri et al. |
| 2007/0178123 A1 | 8/2007 | Levenson et al. |
| 2015/0320101 A1 | 11/2015 | Walton et al. |
| 2016/0052855 A1 | 2/2016 | Bedoukian et al. |

FOREIGN PATENT DOCUMENTS

| | | |
|---|---|---|
| EP | 1 107 730 B1 | 3/2008 |
| EP | 2 090 181 A1 | 8/2009 |
| JP | 2013-021927 A | 2/2013 |
| WO | WO 01/58282 A1 | 8/2001 |
| WO | WO 2007/089652 A2 | 8/2007 |
| WO | WO 2015/048163 A1 | 4/2015 |
| WO | WO 2016/0203 62 A1 | 2/2016 |

OTHER PUBLICATIONS

PubChem [Internet]. Bethesda (MD): National Library of Medicine (US), National Center for Biotechnology Information; 2004-. PubChem Compound Summary for CID 53249445, 4,7-Decadienal, (Z,Z)-; [cited Apr. 21, 2022], Available from: https://pubchem.ncbi.nlm.nih.gov/compound/4_7-Decadienal_-_Z_Z.*

(Continued)

*Primary Examiner* — Leslie A Wong
(74) *Attorney, Agent, or Firm* — Baker Botts L.L.P.

(57) ABSTRACT

Aldehydes of formula (I) (X represents an alkyl or alkenyl group having up to 9 carbon atoms) for use in taste modulation and/or flavor compositions are provided. Specifically, the compounds of the presently disclosed subject matter provide effective and unexpected taste modulating properties. The taste modulation and/or flavor compositions can be incorporated into various consumer end products in particular in combination with high intensity sweeteners.

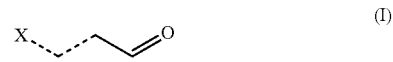

(I)

17 Claims, No Drawings

(56) References Cited

OTHER PUBLICATIONS

Ballini et al., "Solvent Free Synthesis and Deprotection of 1,1-Diacetates Over a Commercially Available Zeolite Y as a Reusable Catalyst," Tetrahedron Letters 39(41):7587-7590 (1998).
Boskou et al., "Content of trans,trans-2,4-decadienal in deep-fried and pan-fried potatoes," European Journal of Lipid Science and Technology 108(2):109-115 (2006).
International Search Report dated Dec. 20, 2017 in International Application No. PCT/US2017/051013.
Kajiwara et al., "Synthesis of 3Z,6Z-Dienoic Acids," Agricultural and Biological Chemistry 41(8):1481-1484 (1977).
Van Lier et al., "Isolation and synthesis of (Z,Z)-4,7-Decadienal, the character impact compound in the oil of *Acorus calamus* L.," Progress in Essential Oil Research: Proceedings of the International Symposium on Essential Oils, pp. 215-225 (1985).

\* cited by examiner

TASTE MODULATING ALDEHYDES

CROSS-REFERENCE TO RELATED APPLICATIONS

This application is a U.S. National Stage Patent Application under 35 U.S.C. § 371 of International Application No. PCT/US2017/051013, filed on Sep. 11, 2017, which claims priority to U.S. Provisional Patent Application Ser. No. 62/385,507, filed Sep. 9, 2016, the contents of each of which are incorporated by reference herein in their entirety.

FIELD

The presently disclosed subject matter relates to compounds capable of modulating the undesirable taste characteristics of high intensity sweeteners, for example, the bitter aftertaste associated with high intensity *Stevia* extract derived sweeteners, and to flavor compositions comprising such compounds. The disclosed subject matter also relates to consumer products comprising such taste modulating compounds and/or flavor compositions.

BACKGROUND

Many consumers desire sweet tasting foods and beverages. However, in many instances consumers are choosing to limit their consumption of caloric sugars (e.g., sucrose, glucose, fructose) as a means to reduce calorie intake and assist in weight loss or for medical reasons requiring such limitation as in the case of diabetes or reactive hypoglycemia. In other instances, there is a desire on the part of the consumers to replace processed refined sugar in their diet with a perceived "less processed" and more "natural" alternative. Thus, there is a strong market demand for low calorie or zero calorie food and beverage options that maintain a sweet taste similar to that achieved through the use of sucrose (i.e., sugar) and other traditional caloric sweeteners.

Alternatives to these traditional sweeteners include "high intensity sweeteners" ("HIS"), which are several times sweeter than sucrose but are either low-calorie or non-caloric. HIS provide an added benefit to food and beverage manufacturers as they are often less expensive and more shelf stable than sugar and can be used in lower amounts than sugar while still providing a comparatively sweet taste profile due to their high sweetening intensity.

Despite these added benefits, use of HIS is often limited due to the undesirable taste characteristics of many HIS. More particularly, HIS are often associated with bitter, astringent, metallic, sour, and/or licorice-like taste characteristics. Therefore, there is a continuing interest in compounds that can increase the perception of a more sugar-like taste and a more uniform sweetness to flavorings and/or consumer products having HIS without the negative characteristics.

In addition to HIS, there are other ingredients used in foods, beverages, oral care products, over the counter (OTC) and prescription pharmaceuticals or other consumer products with undesirable taste characteristics such as bitter, astringent, metallic, sour and/or licorice-like taste characteristics, or combinations thereof. Nonlimiting examples include tannins, caffeic acid or esters thereof, terpenoids, metal salts, active pharmaceutical ingredients (e.g., ibuprofen, dextromethorphan, acetaminophen, guaifenesin, etc.), proteins and peptides, polyphenols (e.g., catechin, epicatechin, epicatechin gallate, gallic acid, epigallocatechin, epigallocatechin gallate, etc.), humulinone, quinine, natural plant extracts, preservatives, vitamins, and minerals. Similarly, there is an ongoing need to identify compounds that can modulate these additional taste characteristics.

Accordingly, it is an object of the presently disclosed subject matter to provide novel compounds and flavor compositions comprising the compounds that can effectively and unexpectedly improve the taste characteristics of HIS. It is another object of the presently disclosed subject matter to provide novel compounds and flavor compositions comprising the compounds that can effectively and unexpectedly modulate other undesirable tasting characteristics of food, beverage, pharmaceutical or other consumer products comprising such ingredients.

SUMMARY OF THE INVENTION

The presently disclosed subject has unexpectedly and surprisingly found compounds that are effective in providing beneficial and desirable taste characteristics.

The presently disclosed subject matter provides a flavor modulating compound represented by Formula I.

wherein the dashed lines can both be single bond or wherein one of the dashed lines is a double bond and the other a single bond, and
wherein X represents a $C_1$-$C_9$ aliphatic or branched alkyl group or a $C_1$-$C_9$ aliphatic or branched alkenyl group which incorporates one or more double bonds.

In certain embodiments, in the flavor modulating compound of Formula (I), the dashed lines can both be a single bond, or one of the dashed lines is a double bond and the other a single bond, and wherein X represents a $C_6$-$C_7$ alkenyl group which incorporates one or more non-conjugated double bonds.

In certain embodiments, the compound is produced by a fermentation and enzyme reaction process.

The presently disclosed subject matter also provides for flavor compositions comprising one or more flavor modulating compounds according to Formula (I). In particular embodiments,
the flavor modulating compound is selected from the group consisting of 4-decenal; 7-decenal; 4,7-decadienal; 2,4,7-decatrienal; 2,6-nonadienal, 3,6-nonadienal; 6-nonenal, and mixtures thereof. In other embodiments, the flavor modulating compound is a mixture of two or more isomers of 4,7-decadienal selected from the group consisting of the (4Z, 7Z)-isomer, the (4E, 7Z)-isomer, the (4Z, 7E)-isomer, the (4E, 7E)-isomer, and mixtures thereof.

The presently disclosed subject matter further provides for consumer products comprising: (a) one or more flavor and/or taste modulating compositions; and (b) a consumer product base. In certain embodiments, the consumer product further comprises at least one high intensity sweetener and/or non-HIS sweetener. In another embodiment, the disclosed subject matter provides a consumer product comprising: (a) one or more compounds according to Formula (I); (b) at least one high intensity sweetener and/or non-HIS sweetener, and (c) a consumer product base.

In certain embodiments, the high-intensity sweetener is selected from the group consisting of 1,2-benzothiazol-3 (2H)-one 1,1-dioxide (saccharin) or its sodium salt; methyl L-α-aspartyl-L-phenylalaninate (aspartame); acesulfame potassium (Ace-K or acesulfame K); 1,6-dichloro-1,6-dideoxy-β-D-fructofuranosyl-4-chloro-4-deoxy-α-D-galactopyranosideneotame (sucralose); (3S)-3-[3-(3-Hydroxy-4-methoxyphenyl)propylamino]-4-[[(2S)-1-methoxy-1-oxo-3-phenylpropan-2-yl]amino]-4-oxobutanoic acid (advantame); (3S)-3-(3,3-Dimethylbutylamino)-4-[[(2S)-1-methoxy-1-oxo-3-phenylpropan-2-yl]amino]-4-oxobutanoic acid (neotame), L-α-aspartyl-N-(2,2,4,4-tetramethyl-3-thietanyl)-D-alaninamide (alitame); sodium N-cyclohexylsulfamate (cyclamate) and its salts (e.g., calcium cyclamate, sodium cyclamate, magnesium cyclamate, potassium cyclamate), and some sugar alcohols (e.g., xylitol) and combinations thereof. In other embodiments, the high intensity sweetener is derived from *Stevia rebaudiana* selected from the group consisting of whole leaf and crude *stevia* extracts, modified *stevia* extracts, mono-, di- and polyglycosylated steviol compounds, green *stevia* powder, Rebaudioside A (Reb A), Rebaudioside B, Rebaudioside C, Rebaudioside D, Rebaudioside D2, Rebaudioside E, and Rebaudioside F, Rebaudioside G, Rebaudioside H, Rebaudioside I, Rebaudioside 1, Rebaudioside K, Rebaudioside L, Rebaudioside M, Rebaudioside N, Rebaudioside O, Rebaudioside Q, Rebaudioside R, Rebaudioside S, Rebaudioside V, Rebaudioside W, Rebaudioside X, Rebaudioside KA, Dulcoside A, Rubusoside, stevioside, and other modified stevioglycosides, and combinations thereof. In other embodiments, the high intensity sweetener is derived from *Siraitia grosvenorii*. such as those selected from the group consisting of modified or unmodified extracts (i.e., Luo Han Go extract or Monk fruit juice) and mogrosides (e.g., mogroside IV, mogroside V, siamenoside 1, and 11-oxo mogroside V). In other embodiments, the high intensity sweetener is selected from the group consisting of methyl L-α-aspartyl-L-phenylalaninate, *Siraitia grosvernorii* extract, Rebaudioside A; and combinations thereof.

The presently disclosed subject matter further provides methods to modulate taste properties of a consumer product, wherein one or more compounds according to Formula (I) is added to the consumer product in an amount effective to modulate the taste profile of the high intensity sweetener.

The presently disclosed subject matter further provides methods for modulating undesirable taste characteristics, such as those resulting from the use of a high intensity sweetener or other ingredient with an undesirable taste profile in a consumer product, comprising adding at least one compound according to Formula (I) to the consumer product containing the high intensity sweetener and/or other ingredient with an undesirable taste profile in an amount sufficient to provide a more desirable taste or flavor profile to the consumer product.

The forgoing has outlined rather broadly the features and technical advantages of the presently disclosed subject matter in order that the detailed description that follows can be better understood. Additional features and advantages of the disclosed subject matter will be described hereinafter which form the subject of the claims of the disclosed subject matter. It should be appreciated by those skilled in the art that conception and specific embodiments disclosed can be readily utilized as a basis for modifying or designing other structures for carrying out the same purpose of the presently disclosed subject matter. It should also be realized by those skilled in the art that such equivalent constructions do not depart from the spirit and scope of the disclosed subject matter as set forth in the appended claims. The novel features which are believed to be characteristics of the disclosed subject matter, both as to its organization and method of operations, together with further objects and advantages will be better understood from the following description.

DETAILED DESCRIPTION

As noted above, there remains a need in the art for compounds that modulate the unpleasant bitter, astringent, metallic, sour, and/or licorice-like taste characteristics associated with HIS and/or other food, beverage, oral care, and/or pharmaceutical product ingredients. The presently disclosed subject matter addresses this need through compounds selected from the group represented by Formula (I) and/or new flavor compositions comprising one or more of the disclosed compounds.

For clarity, and not by way of limitation, the detailed description is divided into the following subsections:
1. Definitions;
2. Taste Modulating Compounds;
3. High Intensity Sweeteners (HIS) and Other Ingredients with Undesirable Taste Profiles;
4. Flavor Compositions; and
5. Use in Consumer Products.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the words "a" or "an" when used in conjunction with the term "comprising" in the claims and/or the specification, can mean "one" but they are also consistent with the meaning of "one or more", "at least one" and/or "one or more than one." Furthermore, the terms "having", "including", "containing", and "comprising" are interchangeable, and one of skill in the art will recognize that these terms are open ended terms.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5% and/or up to 1% of a given value.

As used herein, the teen "isomers" refers to different compounds that have the same molecular formula but differ in arrangement and configuration of the atoms. Also as used herein, the term "stereoisomer" refers to any of the various stereo isomeric configurations which can exist for a given compound of the presently disclosed subject matter and includes geometric isomers. It is understood that a substituent can be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextrorotatory or levorotatory) which they rotate plane polarized light at the wavelength of the sodium D line. The compounds of the presently disclosed subject matter contain one or more asymmetric centers and can thus give rise to enantiomers, diastereomers, and other stereoisomeric forms that can be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers can be prepared using chiral synthons or chiral reagents, or resolved using conventional techniques. If the compound contains a double bond, the substituent can be E or Z configuration. If the compound contains a disubstituted cycloalkyl, the cycloalkyl substituent can have a cis- or trans-configuration. All tautomeric forms are also intended to be included.

As used herein, the terms "flavoring" or "flavor composition" can be used interchangeably and refer to preparations added to a consumer product intended to be imbibed or ingested to impart a taste or flavor profile to the consumer product, or improve, modify or enhance the taste or flavor profile of the consumer product.

As used herein, the term "taste modulation" means modifying the profile of a food, beverage or other ingested consumer product to improve the overall taste experience during consumption, for example, reducing bitterness, improving sweet profile, or improving overall flavor profile and mouthfeel.

As used herein, the term "consumer product" means products intended to be used or consumed in the form in which is it sold, and not intended for subsequent commercial manufacture or modification. Non-limiting examples of consumer products are described in more detail herein.

As used herein, the term "consumer product base" means those components known to those of ordinary skill in the art and used to provide typical properties of the consumer product.

All publications, including but not limited to patents and patent application, cited in this application are herein incorporated by reference as if each individual publication were specifically and individually indicated to be incorporated by reference herein as though fully set forth.

2. Taste Modulating Compounds

The presently disclosed taste modulating compounds include compounds selected from the groups represented by Formula (I).

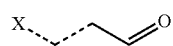
(I)

wherein the dashed lines can both be a single bond, or wherein one of the dashed lines is a double bond and the other a single bond, and wherein X represents a $C_1$-$C_9$ aliphatic or branched alkyl group or a $C_1$-$C_9$ aliphatic or branched alkenyl group, which incorporates one or more double bonds.

In certain embodiments, the compound is Formula I, wherein the dashed lines can both be a single bond, or one of the dashed lines is a double bond and the other a single bond, and wherein X represents a $C_6$-$C_7$ alkenyl group which incorporates one or more non-conjugated double bonds. As such, in certain embodiments, the compounds are $C_9$-$C_{10}$ aldehydes with at least one double bond.

In those embodiments wherein the compounds contain one or more double bonds, each compound can be in the E- or Z-configuration, thereby resulting in various stereoisomeric forms. All such possible isomers, including isomeric mixtures, pure forms, and intermediate mixtures are included in the presently disclosed subject matter.

In certain non-limiting embodiments, the aldehyde compound of Formula (I) is 4-decenal; 7-decenal; 4,7-decadienal; 2,4,7-decatrienal; 6-nonenal, 2,6-nonadienal, or 3,6-nonadienal. In certain embodiments, the aldehyde of Formula (I) is a mixture of two or more isomers of 4,7-decadienal selected from the group consisting of the (4Z, 7Z)-isomer, the (4E, 7Z)-isomer, the (4Z, 7E)-isomer, and the (4E, 7E)-isomer. In another embodiment, the aldehyde is limited to the (4Z, 7Z)-isomer.

The compounds of the present disclosure can be synthetic or naturally derived. Synthetic versions of the compounds include those obtained via chemical synthesis or isolated through chemical processes, whether artificial or nature-identical, such as those described in U.S. Pat. No. 4,687,599, incorporated herein by reference in its entirety. In one embodiment, a synthetic version of a compound of Formula (I) can be prepared as described in Example 9.

Natural versions of the compounds include those obtained via physical, enzymatic and/or microbiological processes, e.g., fermentation, from materials of a plant or animal origin. In one embodiment, a natural version of a compound of Formula (I) can be obtained by extraction of materials of a plant or animal origin. For example, a natural version of 4,7-decadienal can be obtained by extraction of plant material of the species, *Acorus calamus*. In another embodiment, a natural version of a compound of Formula (I) is obtained by fermentation processes, including but not limited to the process described in Example 10.

3. High Intensity Sweeteners (HIS) and Other Ingredients with Undesirable Taste Profiles The compounds of the presently disclosed subject matter can be used in combination with high intensity sweeteners (HIS) or other ingredients with undesirable taste profiles, which can be targets for modulation.

HIS of the presently disclosed subject matter can be synthetic (also referred to herein as "artificial") or naturally derived. Non-limiting examples of synthetic HIS include 1,2-benzothiazol-3(2H)-one 1,1-dioxide (saccharin) or its sodium salt; methyl L-α-aspartyl-L-phenylalaninate (aspartame); acesulfame potassium (Ace-K or acesulfame K); 1,6-dichloro-1,6-dideoxy-β-D-fructofuranosyl-4-chloro-4-deoxy-α-D-galactopyranosideneotame (sucralose); (3S)-3-[3-(3-Hydroxy-4-methoxyphenyl)propylamino]-4-[[(2S)-1-methoxy-1-oxo-3-phenylpropan-2-yl]amino]-4-oxobutanoic acid (advantame); (3S)-3-(3,3-Dimethylbutylamino)-4-[[(2S)-1-methoxy-1-oxo-3-phenylpropan-2-yl]amino]-4-oxobutanoic acid (neotame), L-α-aspartyl-N-(2,2,4,4-tetramethyl-3-thietanyl)-D-alaninamide (alitame); sodium N-cyclohexylsulfamate (cyclamate) and its salts (e.g., calcium cyclamate, sodium cyclamate, magnesium cyclamate, potassium cyclamate), and some sugar alcohols (e.g., xylitol).

Naturally derived HIS can include but are not limited to di-terpene glycosides, such as those sweeteners derived from members of the plant genus, *Stevia*, such as *Stevia rebaudiana*, (also referred to herein as "*Stevia*-derived sweeteners"), or derived from *Siraitia grosvenorii*, also commonly referred to as Luo Han Go or Monk fruit. Non-limiting examples of *Stevia*-derived sweeteners include whole leaf and crude *stevia* extracts, modified *stevia* extracts, mono-, di- and polyglycosylated steviol compounds, green *stevia* powder, Rebaudioside A (Reb A), Rebaudioside B, Rebaudioside C, Rebaudioside D, Rebaudioside D2, Rebaudioside E, and Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Rebaudioside R, Rebaudioside S, Rebaudioside V, Rebaudioside W, Rebaudioside X, Rebaudioside KA, Dulcoside A, Rubusoside, stevioside, and other modified stevioglycosides. Non-limiting examples of *Siraitia grosvenorii* derived HIS include modified or unmodified extracts (i.e., Luo Han Go extract or Monk fruit juice) and mogrosides (e.g., mogroside IV, mogroside V, siamenoside I, and 11-oxo mogroside V).

Other non-limiting examples of naturally derived HIS include sweet proteins (e.g., monatin, curculin, thaumatin, monellin, mabinlin, pentadin, brazzein, hemandulcin, phyllodulcin, glyphyllin, phloridzin, trilobatin, phloretin), neohesperdin dihydrochalcone, naringin dihydrochalcone, glycyrrhizic acid and its salts, polypodoside A, and natural extracts such as licorice root extract, citrus distillates and extracts, and katemfe extract.

Those skilled in the art will recognize that there exist other ingredients used in foods, beverages, over the counter (OTC) and prescription pharmaceuticals or other consumer products having undesirable taste characteristics, such as bitter, astringent, metallic, sour and/or licorice-like taste characteristics, or combinations thereof, that evoke similar off-tastes to the above-mentioned HIS and present similar problems for flavorists. In one embodiment, the presently disclosed compounds can be used to provide taste modulating benefits to such non-HIS materials. Non-limiting examples of such non-HIS modulation target materials include cocoa, coffee, caffeine, theobromine, diketopiperazines, amino acids, bitter peptides, proteins (e.g., Vegetable proteins, casein, soy, whey), hydrolyzed proteins, naringin, taurine, guarana, chlorogenic acid, preservatives (e.g., salts of potassium, salts of sodium), salts of zinc, isoflavones, polyphenols, menthol, quinine, certain essential oils (e.g., mint oils), Maillard reaction products, beer, hops, humulone, isohumulone, humulinone, lupulone, hulupone, tannins, caffeic acid or esters thereof, terpenoids, metal salts, certain active pharmaceutical ingredients (e.g., acetaminophen, ibuprofen, salicylic acid, dextromethorphan, guaifenesin, acetylsalicylic acid, cimetidine, ranitidine, amoxicillin, loperamide), quinidine, quinine, extracts of genetian root, extracts of cinchona bark, polyphenols (e.g., catechin, epicatechin, epicatechin gallate, gallic acid, epigallocatechin, epigallocatechin gallate), omega-3-fatty acids, alcohols, vitamins (e.g., B vitamins), and minerals.

4. Flavor and Taste Modulation Compositions

In certain embodiments, the presently disclosed taste modulating compounds of Formula (I) can be formulated in a "taste modulation composition", to provide taste modulation, but not a particular flavor profile. Such taste modulation compositions can be added to or combined with other flavorings or flavor compositions. In other embodiments, the presently disclosed taste modulating compounds of Formula (I) can be formulated in a "flavor composition", which can be utilized to provide a particular flavor profile in addition to taste modulation. In certain embodiments, the flavor compositions can further contain additional flavor components and/or sweetening components or sweeteners.

In certain embodiments, the taste modulation compositions of the presently disclosed subject matter can comprise additional taste modulation compounds to further modify the taste modulating capabilities of the flavor composition. Non-limiting examples of such taste modulation compounds include terpenes (e.g., sesquiterpenes, diterpenes, triterpenes, etc.), flavonoids, organic acids (such as tartaric acid, acetic acid, citric acid, malic acid, etc.), inorganic acids, organic salts, nucleotide monophosphates, diphosphates, and triphosphates, hydroxyflavanones, hydroxybenzoic acid amides, hydroxydeoxybenzoins, hydroxyphenylalkanediones, diacetyl trimer, γ-aminobutyric acid, vanillin, vanilla extract, divanillins, hydroxyflavans, lactisoles, 2,4-dihydroxybenzoic acid, maltol, ethyl maltol, cyclotene, cyclotene hydrate, furaneol, sotolone, maple furanone, mesifurane, natural distillates and extracts (e.g. honey, molasses, carob, brown sugar, sugar, ginger, green coffee), fatty acids, fatty acid esters, fats, oils, 3-(1-((3,5-Dimethylisoxazol-4-yl)methyl)-1H-pyrazol-4-yl)-1-(3-hydroxybenzyl)-imidazolidine-2,4-dione, lactones, 1-hexadecanol, menthol, menthone, camphor, pulegol, isopulegol, cineole, 2-isopropyl-N-2,3-trimethylbutyramide, N-ethyl-2-isopropyl-5-methylcyclohexane carboxamide, ethyl 3-(p-menthane-3-carboxamido)acetate, N-(4-methoxyphenyl)-p-menthanecarboxamide, N-ethyl-2,2-diisopropylbutanamide, N-cyclopropyl-5-methyl-2-isopropylcyclohexanecarboxamide, N-(1,1-dimethyl-2-hydroxyethyl)-2,2-diethylbutanamide, N-(4-cyanomethylphenyl)-p-menthanecarboxamide, N-(2-(Pyridin-2-yl)ethyl)-3-p-menthanecarboxamide, N-(2-hydroxyethyl)-2-isopropyl-2,3-dimethylbutanamide, cyclopropanecarboxylic acid (2-isopropyl-5-methyl-cyclohexyl)-amide, N-[4-(2-Amino-2-oxoethyl)phenyl]-p-menthanecarboxamide, menthyl pyrrolidone carboxylate, cubebol, icilin, 1-(2-hydroxy-4-methylcyclohexyl)ethanone, N-(4-(cyanomethyl)phenyl)-2-isopropyl-5,5-dimethylcyclohexane-1-carboxamide, 2-isopropyl-5-methylcyclohexyl 4-(dimethylamino)-4-oxobutanoate, N-benzo[1,3]dioxol-5-yl-3-p-menthanecarboxamide, N-benzooxazol-4-yl-3-p-menthanecarboxamide, N-4-([1,2,4]triazol-1-yl)-phenyl-3-p-menthanecarboxamide, N-4-(pyrazol-1-yl)-phenyl-3-p-menthanecarboxamide, N-(1-isopropyl-1,2-dimethylpropyl)-1,3-benzodioxole-5-carboxamide, N-(1-methyl-1-isopropylbutyl)benzamide, fenchyl-N,N-diemethylsuccinamide, fenchyl monosuccinate, ethyl fenchyl malonate, bornyl monosuccinate, isobornyl monosuccinate, menthyl 3-oxobutyrate, menthyl 3-oxopentanoate, 3-1-menthoxypropane-1,2-diol, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutyrate, 6-isopropyl-9-methyl-1,4-dioxaspiro-(4,5)-decane-2-methanol, 2-[(2-p-menthoxy)ethoxy]ethanol, menthyl succinate, menthyl glutarate, dimenthyl succinate, dimenthyl glutarate, menthyl lactate, menthone glycerin ketal, mint oil, peppermint oil, spearmint oil, eucalyptus oil, spilanthol, sanshool, hydroxy γ-sanshool, hydroxy-sanshool, sanshool-I, sanshool II, sanshoamide, Japanese pepper extract, chavicine, echinacea extract, northern prickly ash extract, Nepalese spice timur extract, 4-(1-menthoxymethyl)-2-phenyl-1,3-dioxolane, N-isobutyldeca-(2,4)-dienamide, N-cyclopropyl-(2E,6Z)-nonadienamide, N-ethyl-(2E,6Z)-nonadienamide, jambu oleoresin, allyl-isothiocyanate, 4-hydroxybenzyl isothiocyanate, mustard oil, wasabi extract, elemol, elimicin, lime oxide, elemi oil, ocimene quintoxide, 2-isopropenyl-5-methyl-5-vinyltetrahydrofuran, vanillyl ethyl ether, vanillyl propyl ether, vanillin propylene glycol acetal, ethyl vanillin propylene glycol acetal, capsaicin, gingerol, vanillyl butyl ether, 4-(1-menthoxy-methyl)-2-phenyl-1,3-dioxolane, 4-(1-menthoxy-methyl)-2-(3',4'-dihydroxy-phenyl)-1,3-dioxolane, 4-(1-menthoxy-methyl)-2-(2'-hydroxy-3'-methoxy-phenyl)-1,3-dioxolane, 4-(1-menthoxy-methyl)-2-(4'-methoxyphenyl)-1,3-dioxolane, 4-(1-menthoxy-methyl)-2-(3',4'-methylenedioxy-phenyl)-1,3-dioxolane, black pepper extract, cinnamaldehyde, piperine, hot pepper oil, red pepper oleoresin *capsicum* oleoresin, ginger oleoresin, nonyl acid vanillylamide, 4-(1-menthoxy-methyl)-2-(3'-methoxy-4'-hydroxyphenyl)-1,3-dioxolane, vanillin-1,2-hexylene glycol acetal, vanillin-1,2-butylene glycol acetal, vanillin-1-butoxyglycerol acetal, ethyl vanillin, ethyl vanillyl alcohol (3-ethoxy-4-hydroxybenzyl alcohol), ethyl homovanillate, vanillyl isopropyl ether, and all stereoisomers and mixtures thereof.

In certain embodiments, the additional taste modulation compounds can be compounds known in the art as sweeteners (e.g., sweet proteins) but used at levels below the threshold level necessary to provide a sweetening effect.

In certain embodiments, the presently disclosed taste modulating compounds of Formula (I) can be utilized in a flavor composition comprising at least one HIS and/or at least one non-HIS sweetener. In other embodiments, the flavor composition does not contain HIS and/or non-HIS sweeteners. In still other embodiments, HIS and/or non-HIS sweeteners can be added separately.

The amount of the one or more compounds of Formula (I) present in the flavor composition of the presently disclosed subject matter can vary based on the amount of other modulating agents the flavor composition, but is typically present from about 0.001 part per trillion (ppt) to 10% by weight, or from about one part per trillion to about 10% by weight, or from about 0.001% to about 5% by weight to the total weight of the flavor composition, and values in between. In further embodiments, the compounds of Formula (I) can be present in amounts of from about 0.00001% to about 10% by weight, or from about 0.00001% to about 5% by weight, or from about 0.00001% to about 1% by weight, or from about 0.00001% to about 0.1% by weight of the flavor composition. In other embodiments, the compounds of Formula (I) can be present in amounts of from about 0.00001% to about 10% by weight, or from about 0.0001% to about 10% by weight, or from about 0.001% to about 10% by weight, or from about 0.01% to about 510% by weight, or from about 0.1% to about 10% by weight, or from about 1.0% to about 10% by weight, or from about 5% to about 10% by weight of the flavor composition. In certain embodiments, the compounds of Formula (I) can be present in amounts of from about 0.00001% to about 10% by weight, or from 0.1% to about 5% by weight, or from about 0.5% to about 2% by weight, or from about 0.5% to about 1% of the flavor composition.

In one embodiment of the disclosed subject matter, the taste modulation composition or flavor composition comprises one or more of the compounds of Formula (I) and one or more non-HIS materials. Non-limiting examples of such non-HIS modulation target materials include cocoa, coffee, caffeine, theobromine, diketopiperazines, amino acids, bitter peptides, proteins (e.g., Vegetable proteins, casein, soy, whey), hydrolyzed proteins, naringin, taurine, guarana, chlorogenic acid, preservatives (e.g., salts of potassium, salts of sodium), salts of zinc, isoflavones, polyphenols, menthol, quinine, certain essential oils (e.g., mint oils), Maillard reaction products, beer, hops, humulone, isohumulone, humulinone, lupulone, hulupone, tannins, caffeic acid or esters thereof, terpenoids, metal salts, certain active pharmaceutical ingredients (e.g., acetaminophen, ibuprofen, salicylic acid, dextromethorphan, guaifenesin, acetylsalicylic acid, cimetidine, ranitidine, amoxicillin, loperamide), quinidine, quinine, extracts of genetian root, extracts of cinchona bark, polyphenols (e.g., catechin, epicatechin, epicatechin gallate, gallic acid, epigallocatechin, epigallocatechin gallate), omega-3-fatty acids, alcohols, vitamins (e.g., B vitamins), and minerals.

In yet other embodiments, the disclosed taste modulation compositions or flavor compositions can be incorporated into more complex flavorings containing one or more flavor ingredients or flavor compositions to enhance or compliment the overall taste characteristics of such flavorings. Such flavor ingredients or flavor compositions include, for example, natural or synthetic flavors, i.e., fruit flavors (e.g., lemon, lime, orange, grapefruit; cherry, strawberry, raspberry, cranberry; apple, grape, pineapple, banana, tomato); natural or synthetic botanical flavors, (e.g. tea flavors, coffee flavors, hazelnut, almond, pecan, or other nut flavors, vanilla flavors), and other complex flavor profiles (e.g., cola flavors or imagined flavors, such as "birthday cake" or "ice cream sundae").

The taste modulation or flavor compositions of the presently disclosed subject matter can further comprise one or more support materials. By way of non-limiting example, support materials can include diluents, e.g., ethanol, purified water, glycerol: solvents; carriers, e.g. propylene glycol, triacetin; preservatives, e.g., sulfites, sodium nitrite, propionic acid, sorbic acid, benzoic acid, disodium ethylenediaminetetraacetic acid (EDTA); flavoring agents, e.g., alcohols, esters, aldehydes; ketones, Intones, phenols; flavor enhancers, e.g., monosodium glutamate (MSG), monopotassium glutamate, calcium diglutamate (CDG), guanosine monophosphate disodium guanylate, sodium guanylate, inosinic acid and its salts, L-leucine; antioxidants, e.g., ascorbic acid, sodium ascorbate, calcium ascorbate, fatty acid esters of ascorbic acid, tocopherols, alpha-tocopherol, gamma-tocopherol, delta-tocopherol, propyl gallate, octyl gallate, erythorbic acid, sodium erythorbate, dodecyl gallate, tertiary-butyl hydroquinone (TBHQ), butylated hydroxyanisole (BHA), butylated hydroxytoluene (BHT), citric acid, 4-hexylresorcinol; color retention agents; dyes or lakes; sequestrants, emulsifiers, e.g., lecithins, monoglyceride, acetylated monoglyceride, lactylated monoglyceride, sugar ester, sorbitan ester, polyglycerol ester, calcium stearoyl dilaciate; stabilizers; acids, bases, and/or anticaking agents, e.g., calcium silicate, magnesium carbonate, sodium aluminosilicate. Other known flavor ingredients which are safe for use in products for consumption can be known to those skilled in the art, such as those ingredients listed in reference texts such as S. Arctander, Perfume and Flavor Chemicals, 1969, Montclair, N.J., USA, which is herein incorporated by reference in its entirety.

The presently disclosed taste modulating and/or flavor compositions can be in the form of single ingredients, or simple mixtures of flavoring ingredients or in an encapsulated form, e.g., the composition entrapped into a solid matrix that can include wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate and mixtures thereof. Encapsulation is well-known to persons skilled in the art, and can be performed, for instance, using techniques such as spray-drying, agglomeration or extrusion, or coating encapsulation, including coacervation and complex coacervation techniques. In some embodiments, the taste modulating and/or flavor compositions can be in one or more of the above described forms.

5. Use in Consumer Products

The taste modulation composition or flavor compositions of the presently disclosed subject matter as described above can be advantageously used within a wide variety of consumer products intended to be eaten, imbibed or otherwise consumed.

In certain embodiments, the presently disclosed subject matter further provides a consumer product comprising: (i) a taste modulation or flavor composition comprising at least one compound of Formula (I); and (ii) a consumer product base.

In certain embodiments, the flavor composition comprises at least one HIS and/or other non-HIS sweetener. In other embodiments, the flavor composition does not contain HIS and/or non-HIS sweeteners. In such embodiments, the HIS or non-HIS sweetener can be added separately to the consumer product.

The presently disclosed subject matter also provides a method of modulating taste profile of a consumer product, such method comprising (i) mixing at least one compound of Formula (I) to form a taste modulation composition or flavor composition, and (ii) mixing the taste modulation or flavor composition with a consumer product base.

The compounds of Formula (I) described herein can be employed for their taste modulating properties to benefit a consumer product formulation which can optionally include HIS or other ingredient with undesirable taste characteristics (i.e., consumer product base with HIS or other ingredient with undesirable taste characteristics and optionally, additional formulation components, i.e., support materials, flavors, caloric sweeteners) simply by adding one or more compounds of Formula (I) to the consumer product formulation using conventional techniques and methods. Thus, in an alternative embodiment, the disclosed subject matter also provides a method to improve, enhance or modify the taste properties of a consumer product formulation comprising a HIS or other ingredient with undesirable taste characteristics, wherein at least one compound of Formula (I) is added to the consumer product formulation in an amount effective to modulate the off notes of the consumer product.

In some embodiments, the compounds of Formula (I) are present in the consumer product in an amount less than about 0.1 parts per million (ppm), optionally less than or equal to about 0.01 ppm, optionally less than or equal to about 0.001 ppm, by weight. In some embodiments, the compounds of Formula (I) are present in the consumer product in an amount less than about 0.1 parts per billion (ppb). In other embodiments, the compounds of Formula (I) are present in the consumer product in an amount less than or equal to about 0.10 parts per trillion (ppt) by weight. In specific embodiments, in food and beverage consumer products, the compounds of Formula (I) are present in an amount of about 0.0001 ppt to about 1% by weight.

In yet other embodiments, the compounds of Formula (I) are present in the consumer product in an amount less than their odor detection threshold. In certain embodiments, the compounds of Formula (I) are present in the consumer product in an amount less than the amount at which the flavor characteristics specific to the compounds are detected by the taster.

The amount of HIS and/or non-HIS sweeteners in consumer products varies widely and depends upon the type of consumer product and the desired sweetness impression of the consumer product. In certain embodiments, the consumer product can further comprise one or more natural or synthetic sweeteners (e.g., full caloric sweeteners and/or low caloric sugar substitutes) in addition to the HIS. Non-limiting examples of such natural sweeteners include monosaccharides (e.g., fructose, glucose, mannose, rhamnose, xylose, D-tagatose, tagatose, agalactose, allulose), disaccharides (e.g., sucrose, lactose, maltose), trehalose, galactose, ribulose, threose, arabinose, lyxose, allose, altrose, invert sugar, galacto-oligosaccharides, aldotriose, fructooligosaccharides, tetrasaccharides, mannan-oligosaccharides, malto-oligosaccharides, dextrins, raffinose, sugar alcohols (e.g. erythritol, glycerol, lactitol, maltitol, mannitol, sorbitol, xylitol, galactitol) corn syrup, brown rice syrup, coconut crystals, coconut sugars, coconut syrup, date sugar, fructans, raw honey, maple sap, maple syrup, maple sugar, walnut sap, birch sap, sycamore sap, ironwood sap, molasses, molasses sugar, cane sugar, palm sugar, raw sugar, rice syrup, sorghum, sorghum syrup, cassava syrup, malt syrup, barley malt syrup, barley malt powder, beet sugar, caramel, carob syrup, agave insulin, agave nectar, agave syrup, or mixtures thereof.

Thus, the amount of the one or more compounds and/or taste modulation compositions and/or flavor compositions of the presently disclosed subject matter in the consumer product will correspondingly vary depending upon the amount of HIS sweeteners in the consumer product, as well as the amounts and types of the other component ingredients of the consumer product, including any additional sweeteners. These and other factors will influence the determination of the amount of the presently disclosed compounds in a consumer product comprising a HIS which is effective to modulate the unpleasant taste characteristics of the HIS. Based upon such factors and the teachings of this disclosure, those skilled in the art of formulating flavorings and/or consumer products can ascertain the appropriate and effective amount of the one or more compounds and/or one or more taste modulation compositions and/or one or more flavor compositions of the presently disclosed subject matter to add to modulate the off notes of the HIS in a consumer product.

In one embodiment of the disclosed subject matter, the consumer product containing the taste modulation composition or flavor composition having one or more of the compounds of Formula (I) can further comprise one or more high intensity sweeteners selected from the group consisting of: 1,2-benzothiazol-3(2H)-one 1,1-dioxide (saccharin) or its sodium salt; methyl L-α-aspartyl-L-phenylalaninate (aspartame); acesulfame potassium (Ace-K or acesulfame K);

1,6-dichloro-1,6-dideoxy-β-D-fructofuranosyl-4-chloro-4-deoxy-α-D-galactopyranosideneotame (sucralose); (3S)-3-[3-(3-Hydroxy-4-methoxyphenyl)propylamino]-4-[[(2S)-1-methoxy-1-oxo-3-phenylpropan-2-yl]amino]-4-oxobutanoic acid (advantame); (3S)-3-(3,3-Dimethylbutylamino)-4-[[(2S)-1-methoxy-1-oxo-3-phenylpropan-2-yl]amino]-4-oxobutanoic acid (neotame), L-α-aspartyl-N-(2,2,4,4-tetramethyl-3-thietanyl)-D-alaninamide (alitame); sodium N-cyclohexylsulfamate (cyclamate) and its salts (e.g., calcium cyclamate, sodium cyclamate, magnesium cyclamate, potassium cyclamate), and some sugar alcohols (e.g., xylitol), and combinations thereof.

In a further embodiment of the disclosed subject matter, the consumer product containing the taste modulation composition or flavor composition having one or more of the compounds of Formula (I) can further comprise one or more di-terpene glycosides, such as *Stevia*-derived sweeteners, selected from the group consisting of whole leaf and crude *stevia* extracts, modified *stevia* extracts, mono-, di- and polyglycosylated steviol compounds, green *stevia* powder, Rebaudioside A (Reb A), Rebaudioside B, Rebaudioside C, Rebaudioside D, Rebaudioside D2, Rebaudioside E, and Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Rebaudioside R, Rebaudioside S, Rebaudioside V, Rebaudioside W, Rebaudioside X, Rebaudioside KA, Dulcoside A, Rubusoside, stevioside, and other modified stevioglycosides; or sweeteners derived from *Siraitia grosvenorii*. such as those selected from the group consisting of modified or unmodified extracts (i.e., Luo Han Go extract or Monk fruit juice) and mogrosides (e.g., mogroside IV, mogroside V, siamenoside I, and 11-oxo mogroside V).

In another embodiment of the disclosed subject matter, the consumer product contains a taste modulation composition or flavor composition having at least one of the presently disclosed compounds of Formula (I) and further comprises an extract of *Siraitia grosvenorii*, optionally (4Z, 7Z)-decadienal and an extract of *Siraitia grosvenorii*.

In still another embodiment of the disclosed subject matter, the consumer product contains a taste modulation composition or flavor composition having at least one of the presently disclosed compounds of Formula (I) and further comprises methyl L-α-aspartyl-L-phenylalaninate, and optionally (4Z, 7Z)-decadienal and methyl L-α-aspartyl-L-phenylalaninate.

In yet another embodiment of the disclosed subject matter, the consumer product contains a taste modulation composition or flavoring composition having at least one of the presently disclosed compounds of Formula (I) and further comprises 1,2-benzothiazol-3(2H)-one 1,1-dioxide (saccharin) or its sodium salt, optionally (4Z, 7Z)-decadienal and 1,2-benzothiazol-3(2H)-one 1,1-dioxide (saccharin) or its sodium salt.

In still another embodiment of the disclosed subject matter, the consumer product contains a taste modulation composition or flavoring composition having at least one of the presently disclosed compounds of Formula (I) and further comprises acesulfame potassium, optionally (4Z, 7Z)-decadienal and acesulfame potassium.

In a further embodiment of the disclosed subject matter, the consumer product contains a taste modulation composition or flavoring composition having at least one of the presently disclosed compounds of Formula (I) and further comprises 1,6-dichloro-1,6-dideoxy-β-D-fructofuranosyl-4-chloro-4-deoxy-α-D-galactopyranosideneotame, optionally (4Z, 7Z)-decadienal and 1,6-dichloro-1,6-dideoxy-β-D-fructofuranosyl-4-chloro-4-deoxy-α-D-galactopyranosideneotame.

In a yet further embodiment of the disclosed subject matter, the consumer product contains a taste modulation composition or flavoring composition having at least one of the presently disclosed compounds of Formula (I) and further comprises (3S)-3-[3-(3-Hydroxy-4-methoxyphenyl)propylamino]-4-[[(2S)-1-methoxy-1-oxo-3-phenylpropan-2-yl]amino]-4-oxobutanoic acid, optionally (4Z, 7Z)-decadienal and (3S)-3-[3-(3-Hydroxy-4-methoxyphenyl)propylamino]-4-[[(2S)-1-methoxy-1-oxo-3-phenylpropan-2-yl]amino]-4-oxobutanoic acid.

In a still further embodiment of the disclosed subject matter, the consumer product contains a taste modulation composition or flavoring composition having at least one of the presently disclosed compounds of Formula (I) and further comprises (3S)-3-(3,3-Dimethylbutylamino)-4-[[(2S)-1-methoxy-1-oxo-3-phenylpropan-2-yl]amino]-4-oxobutanoic acid (neotame), optionally (4Z, 7Z)-decadienal and (3S)-3-(3,3-Dimethylbutylamino)-4-[[(2S)-1-methoxy-1-oxo-3-phenylpropan-2-yl]amino]-4-oxobutanoic acid.

In certain other embodiments, the consumer product comprises at least one non-HIS ingredient with undesirable taste characteristics. In yet further embodiments, the non-HIS ingredient with undesirable taste characteristics can be added separately to the consumer product. Such non-HIS ingredients with undesirable taste characteristics include but are not limited to cocoa, coffee, caffeine, theobromine, diketopiperazines, amino acids, bitter peptides, proteins (e.g., Vegetable proteins, casein, soy protein), hydrolyzed proteins, naringin, taurine, guarana, chlorogenic acid, preservatives (e.g., salts of potassium, salts of sodium), salts of zinc, isoflavones, polyphenols, menthol, quinine, certain essential oils (e.g., mint oils), Maillard reaction products, beer, hops, humulone, isohumulone, humulinone, lupulone, hulupone, tannins, caffeic acid or esters thereof, terpenoids, metal salts, certain active pharmaceutical ingredients (e.g., acetaminophen, ibuprofen, salicylic acid, dextromethorphan, guaifenesin, acetylsalicylic acid, cimetidine, ranitidine, amoxicillin, loperamide), quinidine, quinine, extracts of genetian root, extracts of cinchona bark, polyphenols (e.g., catechin, epicatechin, epicatechin gallate, gallic acid, epigallocatechin, epigallocatechin gallate), omega-3-fatty acids, alcohols, vitamins (e.g., B vitamins), and minerals.

The amount of the one or more compounds and/or taste modulation compositions and/or flavor compositions of the presently disclosed subject matter in the consumer product will correspondingly vary depending upon the amount of ingredients with undesirable taste characteristics in the consumer product, as well as the amounts and types of the other component ingredients of the consumer product. These and other factors will influence the determination of the amount of the presently disclosed compounds in a consumer product comprising ingredients with undesirable taste characteristics which is effective to modulate the taste profile of the consumer product. Based upon such factors and the teachings of this disclosure, those skilled in the art of formulating flavorings and/or consumer products can ascertain the appropriate and effective amount of the one or more compounds and/or one or more taste modulation compositions and/or one or more flavor compositions of the presently disclosed subject matter to modulate the taste profile of the consumer product.

Exemplary consumer products of the presently disclosed subject matter include food products, e.g., baked goods, sauces, soups, snack foods, confectionary products, dairy products, baby foods, condiments and preserves; beverages; oral care products; pharmaceuticals; pet food; and animal feed. This list of products is given by way of illustration and is not to be regarded as being in any way limiting.

Non-limiting examples of beverages, e.g., ready-to-drink beverages, beverage concentrates, include carbonated and non-carbonated soft drinks, frozen ready-to-drink beverages, coffee beverages, tea beverages, dairy beverages, powdered soft drinks, flavored waters, enhanced waters, sports drinks, fruit juice and fruit-juice flavored drinks, wine coolers, alcoholic and non-alcoholic ready-to-drink cocktails, and flavored alcoholic beverages. Such beverages can optionally contain a flavor, natural or synthetic. A particular class of beverages for which the present compositions and methods are useful is diet soft drinks (or sodas), such as colas, citrus and fruit flavored beverages, and the like. In some embodiments, the consumer product is a concentrated flavoring product to be used by the consumer to flavor water or another beverage, e.g., a flavor packet, flavor tablet or flavor enhancer drops.

In certain embodiments, the consumer product of the presently disclosed subject matter is a baked good. "Baked goods" as used herein includes ready-to-eat products, ready-to-bake products, flours, and mixes requiring preparation before serving. Non-limiting examples of baked goods include cakes, crackers, cookies, brownies, muffins, rolls, bagels, donuts, pies, strudels, pastries, croissants, biscuits, bread, bread products, and buns.

Non-limiting examples of confectionary products include chewing gums, hard candies, chewy candies, caramels, gummy candies, and chocolates. Non-limiting examples of dairy products include ice cream, puddings, and yogurts. Non-limiting examples of condiments and preserves include syrups, marinades, dips, seasonings, ketchup, salad dressings, and fruit preserves and preparations. Non-limiting examples of cereals and bars include breakfast cereals, breakfast bars, protein bars, granola bars, cereal coatings, and oatmeal.

In certain embodiments, the composition of the disclosed subject matter can be used in pharmaceutical products such as cough syrups or other liquid pharmaceutical formulations, chewable tablets or pharmaceutical dosage forms in the form of an inhaled mist, a "candy", chewable gum, or hard lozenge. Non-limiting examples of oral care products include pharmaceuticals, e.g., throat lozenges, vitamins, chewables, nebulizers, medicinal drops, toothpaste, tooth gel, oral wash, mouth rinse, mouthwash, oral film strips, and breath mints. Non-limiting examples of pharmaceuticals include decongestants, cough mixtures, throat lozenges, indigestion preparations, oral analgesics, tablets, capsules, drops, etc. In some embodiments, compositions of the presently disclosed subject matter can be added, directly or indirectly, to a pharmaceutical dosage form, such as a tablet, capsule, drop or lozenge, that also contains a therapeutically active agent. The compositions of the disclosed subject matter can be added to improve the taste properties of the formulations disclosed in International Published Application No. WO 2007/089652, which is hereby incorporated by reference in its entirety.

In another embodiment, a composition of the disclosed subject matter is added, directly or indirectly, to a pharmaceutical dosage form (e.g., a tablet, capsule, drop, lozenge or syrup) that contains a therapeutically active agent (e.g., a medicament such as dextromethorphan or other antitussive drugs). For example, one embodiment of the disclosed subject matter provides a cough drop or lozenge containing a composition of the disclosed subject matter.

In certain embodiments, a composition of the disclosed subject matter can be combined with therapeutically active agents including, for example, analgesics, such as ibuprofen and acetaminophen; laxatives, such as phenolphthalein dioctysodiumsulfosuccinate; anorexics, such as amphetamines and phenylpropanolamine; antacids, such as calcium carbonate; antiasthmatics, such as theophylline; antidiarrheics, such as diphenoxylate hydrochloride; antiflatulents such as simethecon; antimigraine agents such as ergotamine tartarate; antipsychotics, such as haloperidol; antispasmodics or sedatives, such as phenobarbital (with or without atropine); antihyperactive agents, such as methyldopa and methylphenidate; tranquilizers, such as benzodiazepines, hydroxyzine meprobamates and phenothiazines; antihistaminic agents, such as chlorpheniramine maleate, pyrilamine maleate, doxylamine succinate, brompheniramine maleate, phenyltoloxamine citrate, chlorcyclizine hydrochloride and pheniramine maleate; decongestants such as phenylpropanolamine HCl, phenylephrine HCl, phenylpropanolamine bitartrate, and the sulfate or hydrochloride of pseudoephedrine; beta blockers, such as propranolol; anti-alcoholism agents, such as disulfiram; cough suppressants, such as benzocaine and dextromethorphan; fluoride supplements, such as sodium fluoride; local antibiotics, such as tetracycline and cleocin; corticosteroid suppliers, such as prednisone/prednisolone; anti-goiter agents, such as colchicine and allopurinol; anti-epileptics, such as phenytoin sodium; anti-dehydration agents, such as electrolyte supplements; antiseptics, such as cetyl pyridinium chloride; anticavity agents, such as urea; and the like.

In certain embodiments, the compositions of the disclosed subject matter are included in pharmaceutical dosage forms (e.g., chewing gums or lozenges) containing nicotine in order to modulate the bitter and irritating taste of nicotine. In many commercial products designed for smoking cessation, nicotine is present in the form of nicotine polacrilex. Nicotine polacrilex is nicotine bound to an ion-exchange resin such as a weak acid, polacrilex resin having a polymethacrylic acid/divinybenzene polymer matrix and having a hydrogen ion form. Commercial examples of ion exchange resins include Amberlite™ IRP64 (available from Rohm and Haas, now Dow Chemical Co., Midland, Mich.) and Purolite™ C115HMR (available from The Purolite Co., Bala Cynwyd, Pa.). An exemplary commercial product, Commit®, is commercially available from GlaxoSmithKline (Middlesex UK) as a dissolvable lozenge containing either 2 mg or 4 mg of nicotine.

Chewing gums and lozenges containing nicotine are also commercially available under the trade name Nicorette® (e.g., Nicorette® White Ice™ Mint), Nicotinell®, and non-branded, generic versions of the same. These formulations typically contain 2 mg or 4 mg of nicotine per unit serving. The compositions of the disclosed subject matter can be used to improve the properties of the formulations disclosed in U.S. Published Application No. 2007/0014887, or EP Published Application EP 1 107 730, each of which is hereby incorporated by reference in its entirety.

In certain embodiments, the consumer product is a concentrate sweetener. Non-limiting examples of suitable concentrate compositions include syrups and tabletop sweeteners in powdered or tablet form. In one exemplary embodiment, the consumer product is provided in the form of multiple, single-serving packages or packets in which the sweetener can be stored, distributed and used. Optionally, the concentrate sweetener composition can include one or more natural flavorings.

In certain other embodiments, the consumer product is animal feed or household pet food, including animal health and nutrition products. Non-limiting examples of such animal feed and pet foods include compound feed, liquid feed, feedstuff (e.g., premixes, feed rations, protein or mineral supplements), wet or dry canine food, dog biscuits or treats, and wet or dry feline food.

The disclosed subject matter also provides a method for modulating the taste characteristics of a high intensity sweetener comprising adding at least one compound of the presently disclosed subject matter to the sweetener in an amount sufficient to provide a taste profile closer to the taste profile provided through the use of sucrose.

In one embodiment of the disclosed subject matter, the consumer product comprises at least one of the presently disclosed compounds and aspartame. Non-limiting examples of such consumer products include diet soda and other soft drinks, juices, wine coolers, cocoa mixes, teas, instant coffees, milk drinks, shake mixes, yogurt, table top sweeteners, instant breakfasts, breakfast cereals, frozen desserts, gelatin desserts, puddings, topping mixes, chewing gum, breath mints, laxatives, and chewable vitamin supplements.

In another embodiment of the disclosed subject matter, the consumer product comprises at least one of the presently disclosed compounds and one or more Stevia derived sweeteners. In yet another embodiment of the disclosed subject matter, the consumer product comprises (4Z, 7Z)-decadienal and Rebaudioside A. Non-limiting examples of consumer products for which this embodiment is particularly well-suited include beverage products (diet soda and other soft drinks, flavored waters), yogurt, cereal, chewing gum, soft and hard candies, table top sweeteners, and pharmaceutical products. In a further embodiment of the disclosed subject matter, the consumer product comprises at least one of the presently disclosed compounds and an extract of Siraitia grosvenorii.

In still another embodiment of the disclosed subject matter, the consumer product comprises at least one of the presently disclosed compounds and methyl L-α-aspartyl-L-phenylalaninate, optionally (4Z, 7Z)-decadienal and methyl L-α-aspartyl-L-phenylalaninate. Non-limiting examples of suitable consumer products include diet soda and other soft drinks, juices, wine coolers, cocoa mixes, teas, instant coffees, milk drinks, shake mixes, yogurt, table top sweeteners, instant breakfasts, breakfast cereals, frozen desserts, gelatin desserts, puddings, topping mixes, chewing gum, breath mints, laxatives, and chewable vitamin supplements.

In still another embodiment of the disclosed subject matter, the consumer product comprises at least one of the presently disclosed compounds and 1,2-benzothiazol-3(2H)-one 1,1-dioxide (saccharin) or its sodium salt, optionally (4Z, 7Z)-decadienal and 1,2-benzothiazol-3(2H)-one 1,1-dioxide (saccharin) or its sodium salt. Non-limiting examples of suitable consumer products include beverages, table top sweeteners, In still another embodiment of the disclosed subject matter, the consumer product comprises at least one of the presently disclosed compounds and acesulfame potassium, optionally (4Z, 7Z)-decadienal and acesulfame potassium. Non-limiting examples of suitable consumer products include baked goods, frozen desserts, candies, and beverages.

In yet another embodiment of the disclosed subject matter, the consumer product comprises at least one of the presently disclosed compounds and 1,6-dichloro-1,6-optionally, (4Z, 7Z)-decadienal and 1,6-dichloro-1,6-dideoxy-β-D-fructofuranosyl-4-chloro-4-deoxy-α-D-galactopyranoside-neotame. Non-limiting examples of suitable consumer products include baked goods, beverages, chewing gum, gelatins, and frozen dairy desserts.

In a further embodiment of the disclosed subject matter, the consumer product comprises at least one of the presently disclosed compounds and (3S)-3-[3-(3-Hydroxy-4-methoxyphenyl)propylamino]-4-[[(2S)-1-methoxy-1-oxo-3-phenylpropan-2-yl]amino]-4-oxobutanoic acid, optionally (4Z, 7Z)-decadienal and (3S)-3-[3-(3-Hydroxy-4-methoxyphenyl)propylamino]-4-[[(2S)-1-methoxy-1-oxo-3-phenylpropan-2-yl]amino]-4-oxobutanoic acid. Non-limiting examples of particularly suitable consumer products include baked goods.

In a yet further embodiment of the disclosed subject matter, the consumer product comprises at least one of the presently disclosed compounds and (3S)-3-(3,3-Dimethylbutylamino)-4-[[(2S)-1-methoxy-1-oxo-3-phenylpropan-2-yl]amino]-4-oxobutanoic acid (neotame), optionally (4Z, 7Z)-decadienal and (3S)-3-(3,3-Dimethylbutylamino)-4-[[(2S)-1-methoxy-1-oxo-3-phenylpropan-2-yl]amino]-4-oxobutanoic acid. Non-limiting examples of particularly suitable consumer products include baked goods.

In another aspect, the presently disclosed subject matter provides a method to modulate the taste characteristics of a consumer product comprising one or more bitter, astringent, metallic or other undesirable flavor characteristics by adding to the base of the consumer product an effective quantity of at least one compound of Formula (I) and/or a taste modulation composition comprising at least on compound of Formula (I) and/or a flavor composition comprising at least on compound of Formula (I). As used herein, the term "effective quantity" means the amount of said compounds of Formula (I) and/or a taste modulation composition comprising at least on compound of Formula (I) and/or flavor composition comprising at least one compound of Formula (I) in a consumer product capable of imparting a less unpleasant taste profile to the product. The effective quantity will vary widely depending on the other ingredients present, their relative amounts, and the desired effect.

EXAMPLES

The presently disclosed subject matter will be better understood by reference to the following Examples, which are provided as exemplary of the disclosed subject matter, and not by way of limitation.

Example 1: Flavor Composition (Rebaudioside A) Taste Improvement

Two flavor compositions for taste comparison were prepared according to the following table:

TABLE 1

|  | Control | A |
|---|---|---|
| Water | 99.97% | 99.47% |
| Rebaudioside A 97% (PureCircle ®) | 0.03% | 0.03% |
| 0.1 parts per billion (ppb) solution of (4Z,7Z)-decadienal in ethanol | — | 0.5% |

Percentages shown are by weight. Three trained expert panelists evaluated the two sweetening flavor compositions. All three indicated Flavor Composition A was much cleaner with a significantly better after-taste than the Control.

Example 2: Flavor Composition (Methyl L-α-Aspartyl-L-Phenylalaninate) Taste Improvement Two flavor compositions for taste comparison were prepared according to the following table:

TABLE 2

|  | Control | A |
| --- | --- | --- |
| Water | 99.98% | 99.97% |
| methyl L-α-aspartyl-L-phenylalaninate | 0.02% | 0.02% |
| 10 ppb solution of (4Z,7Z)-decadienal in ethanol | — | 0.01% |

Percentages shown are by weight. Three trained expert panelists evaluated the two sweetening flavor compositions. All three indicated Flavor Composition A had a significantly better after-taste than the Control.

Example 3: Flavor Composition (*Siraitia grosvenorii* Extract) Taste Improvement Two flavor compositions for taste comparison were prepared according to the following table:

TABLE 3

|  | Control | A |
| --- | --- | --- |
| Water | 98.5% | 98.4% |
| *Siraitia grosvenorii* ("Monkfruit") juice | 1.5% | 1.5% |
| 10 ppb solution of (4Z,7Z)-decadienal in ethanol | — | 0.10% |

Percentages shown are by weight. Three trained expert panelists evaluated the two sweetening flavor compositions. All three indicated Flavor Composition A had a significantly better after-taste than the Control.

Example 4: Chewing Gum Taste Improvement

Three chewing gum samples were prepared for taste comparison: (1) a Control sample without any taste modulating components; (2) Sample A comprising a commercial modulation flavoring composition for modulating undesirable HIS taste characteristics; and (3) Sample B in which 0.1% of the solvent in the commercial taste modulation flavoring composition of Sample A was substituted with 0.1% of (4Z, 7Z)-decadienal to produce a "Modulation Flavoring Including Taste Modulating Compound", all as shown in Table 4. "Chewing Gum Base Components" are components known to those of ordinary skill in the art and used to provide typical chewing gum properties and include elastomers (e.g., polyisobutylene, polybutylene, isobutylene-isoprene co-polymers, styrene-butadiene co-polymers, polyvinylacetate, natural rubber, jelutong, lechi caspi, perillo); elastomer plasticizers (e.g., glycerol ester of partially hydrogenated rosin, glycerol esters of tall oil rosin, methyl and partially hydrogenated methyl esters of rosin); waxes (e.g., polyethylene, bees wax, carnauba, paraffin); fats, oils, emulsifiers, fillers (e.g., calcium carbonate, magnesium carbonate, aluminum hydroxide, magnesium and aluminum silicates, clay, alumina, cellulose polymers); texturizers (e.g., hydrogenated and partially hydrogenated vegetable oils, glycerol monostearate, cocoa butter, palmitic acid, oleic acid, linolenic acid).

TABLE 4

|  | Control | Sample A | Sample B |
| --- | --- | --- | --- |
| Chewing Gum Base Components | 99.6% | 99.5% | 99.5% |
| Rebaudioside A 97% (PureCircle ®) | 0.4% | 0.4% | 0.4% |
| Commercial Taste Modulation Flavoring | — | 0.1% | — |
| Modulation Flavoring Including Taste Modulating Compound | — | — | 0.1% |

Percentages shown are by weight. Over the course of separate tasting sessions, a total of twenty trained expert panelists evaluated the three chewing gum samples and found Sample B provided better after-taste than either the Control or Sample A.

Example 5: Yogurt Improvement

Samples were prepared to evaluate the effect of a modulating composition containing (4Z, 7Z)-decadienal with a reduced sugar *Stevia* sweetened yogurt.

A reduced sugar yogurt base (control) was prepared with 7.5% sugar, 68 ppm Reb A 97 and nonfat plain yogurt. The test sample was the control plus 0.05% of the modulating composition. The modulating composition contained 0.0001% of a 0.01% cut of (4Z, 7Z)-decadienal in conjunction with other modulating agents. Sensory evaluation was carried out by an expert panel of 5 people.

All 5 panelists indicated the test sample had less lingering off-taste than the control. Two panelists indicated the test sample was creamier than control. One panelist noted an improved sweet profile.

Example 6: Monkfruit Juice Taste Improvement

A taste comparison was conducted by combining and mixing 0.000001% cut of 1% 2,6-nonadienal (I % in ethanol) in ethyl acetate and used that dilution at 0.10% in a Monkfruit beverage in water, wherein Monkfruit juice concentrate was present at 0.15%. Three trained experts evaluated the combination against a control of Monkfruit juice without the taste modulation compound. The resulting combination demonstrated a modulation of the off-notes, i.e., undesirable taste profile, of the Monkfruit juice.

Examples 7 and 8 provide exemplary embodiments of additional low calorie food and beverage products in accordance with the presently disclosed subject matter.

Example 7: Flavored Water Beverage

AceK and a 1 parts per trillion dilution of (4Z, 7Z)-decadienal in ethanol are combined and then mixed with a natural strawberry flavoring. The resulting mixture is added to treated water.

Example 8: Low Calorie Baked Good (Cookie) with Concentrated Sweetener

Rebaudioside A 97% and (4Z, 7Z)-decadienal are mixed to form a concentrated sweetener. Cookies are prepared by blending the concentrated sweetener with salt, sugar, baking soda, flavor, and shortening/butter. Eggs and then flour are added to the mixture to make cookie dough. The cookies are dropped by measured amount (approximately a teaspoon amount) onto a cookie sheet and baked at 420 degrees Fahrenheit for 8 minutes.

Example 9: Synthesis of 4Z, 7Z-decadienal

Synthesis of cis-3-hexenyltriphenylphosphonium bromide (2 steps from cis-3-hexenol): Under a blanket of $N_2$, cis-3-hexenol (0.4 mol), THF (s/s=10) and triethylamine (2 eq.) were combined and cooled to 0° C. Methanesulfonyl chloride (1.5 eq.) was added drop-wise by addition funnel. Thirty minutes after the addition of the chloride, GC of the reaction mixture showed no starting material. The reaction mixture was poured in to diethyl ether, washed with 10% HCl, then brine, then saturated NaHCO$_3$, then brine again. The organic material was dried over MgSO$_4$ and concentrated to an orange oil. The crude cis-3-hexenylmesylate, without further purification, was diluted in diethyl ether (s/s=10) and added drop-wise to a solution of lithium bromide (1.5 eq.) and diethyl ether (s/s=4) at room temperature. After stirring overnight, the reaction mixture was poured into brine. The organic phase was separated and the aqueous phase extracted with diethyl ether 3 times. The ether extracts were dried over MgSO$_4$ and concentrated to crude cis-3-hexenylbromide, which could be used as is for the following step. Cis-3-hexenylbromide was diluted with acetonitrile (s/s=10), combined with PPh$_3$ (1.5 eq.) and refluxed for 36 hours. After removing acetonitrile under reduced pressure, a 1:1 mixture of hexanes:diethyl ether was added to the reaction flask and refrigerated overnight. The resulting solid was filtered and washed with diethyl ether until a sample of the solid showed no more PPh$_3$ by $^1$H NMR. After drying under vacuum, pure cis-3-hexenyltriphenylphosphonium bromide was collected.

Synthesis of 3-(1,3-dioxolan-2-yl)propanal

Acrolein ethylene acetal was combined with toluene (s/s=1), Rh(CO)$_2$Acac (0.0015 eq.) and PPh$_3$ (0.0078 eq.) in an autoclave. CO/H$_2$ (1:1) was added to the reactor at 250 psi and the contents of the vessel stirred at 65° C. After 48 hours the reaction was complete, giving a mixture of approximately 50/50 branched/linear products. Toluene and low-boiling impurities were removed by distillation (20T, 35° C. bath, 24° C. bulb). Fractional distillation (3-ft column, r/r=12/1, 0.78T, 65° C. bath, 52° C. bulb) removed most of the branched product. Then, short path distillation (0.88 T, 65° C. bath, 36° C. bulb) provided the pure linear product 3-(1,3-dioxolan-2-yl)propanal.

Synthesis of 2-((3Z,6Z)nona-3,6-dienyl)-1,3-dioxolane 3-(1,3-dioxolan-2-yl)propanal was then used for a Wittig reaction. Specifically, cis-3-hexenyltriphenylphosphonium bromide (1 eq.) was added to a round bottom flask equipped with an addition funnel. After evacuating the flask and purging with N$_2$, diethyl ether (s/s=2) was added to form a slurry with the salt. At room temperature, n-BuLi (1.6M in hexanes, 1 eq.) was added to the slurry over one hour drop-wise, and stirred for an additional hour to form the ylide. The reaction was cooled to −35° C. on a bath of acetone with dry ice. 3-(1,3-Dioxolan-2-yl)propanal (1 eq.) in diethyl ether (s/s=10) was then added drop-wise to the ylide. The reaction was allowed to warm to room temperature and stirred overnight. Saturated NH$_4$Cl was added to the reaction mixture and stirred until all solid was dissolved. The mixture was extracted 3 times with diethyl ether, washed with 5% HCl, then saturated NaHCO$_3$, then brine. The ether extracts were dried over MgSO$_4$ and concentrated. The concentrated extracts were filtered with a mixture of 1:1 diethyl ether:hexanes. The filtrate was concentrated, and after bulb-to-bulb distillation (0.5 T, up to 110° C.), the product was obtained.

Deprotection of 2-((3Z,6Z)nona-3,6-dienyl)-1,3-dioxolane to Obtain 4Z, 7Z-decadienal 2-(3Z,6Z)Nona-3,6-dienyl)-1,3-dioxolane was heated to 75° C. with 50% glyoxylic acid (s/s=2) and 1,4-dioxane (s/s=2) overnight. After cooling, the reaction mixture was treated with 5% Na$_2$CO$_3$, extracted with diethyl ether, washed with water, dried and concentrated to crude 4Z, 7Z-decadienal. Fractional distillation (0.44 T, 35-36° C.) gave 4Z,7Z-decadienal.

Example 10: Fermentation Process for the Synthesis of 4Z, 7Z-decadienal

A natural version of 4,7-decadienal is obtained by first treating eicosapentaenoic acid (EPA) with *Thalassiosira rotula* diatoms, which is grown for 3 weeks at 20° C. under carbon dioxide using a 13:11 light:dark cycle in L1 medium. The cells are harvested and frozen, then milled in additional L1 medium. EPA is then added to these milled cells in neutral buffer at room temperature and stirred for 3 hours. The sample is extracted with ethyl acetate and analyzed by gas chromatography, which confirmed the presence of 2,4, 7-decatrienal. This product is then treated with *Saccharomyces cerevisiae* yeast and D-glucose in pH 7.5 buffer at 30° C. for 10 minutes. The crude fermentation product is extracted with ethyl acetate and analyzed by gas chromatography, which confirms the presence of the desired 4,7-decadienal.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

From the foregoing description, various modifications and changes in the compositions and methods will occur to those skilled in the art. All such modifications coming within the scope of the appended claims are intended to be included therein.

Patents, patent applications publications product descriptions, and protocols are cited throughout this application the disclosures of which are incorporated herein by reference in their entireties for all purposes.

What is claimed is:
1. A consumer product comprising: (a) a flavor or taste modulating composition comprising (4Z,7Z)-decadienal; (b) at least one high intensity sweetener; and (c) a consumer product base, wherein (4Z,7Z)-decadienal is added to the consumer product in an amount of from about 0.0001 ppt to about 1% by weight.

2. The consumer product of claim 1, wherein the high intensity sweetener is selected from the group consisting of 1,2-benzothiazol-3(2H)-one 1,1-dioxide (saccharin) or its sodium salt; methyl L-α-aspartyl-L-phenylalaninate (aspartame); acesulfame potassium (Ace-K or acesulfame K); 1,6-dichloro-1,6-dideoxy-β-D-fructofuranosyl-4-chloro-4-deoxy-α-D-galactopyranosideneotame (sucralose); (3S)-3-[3-(3-Hydroxy-4-methoxyphenyl)propylamino]-4-[[(2S)-1-methoxy-1-oxo-3-phenylpropan-2-yl]amino]-4-oxobutanoic acid (advantame); (3S)-3-(3,3-Dimethylbutylamino)-4-[[(2S)-1-methoxy-1-oxo-3-phenylpropan-2-yl]amino]-4-oxobutanoic acid (neotame), L-α-aspartyl-N-(2,2,4,4-tetramethyl-3-thietanyl)-D-alaninamide (alitame); sodium N-cyclohexylsulfamate (cyclamate), calcium cyclamate, sodium cyclamate, magnesium cyclamate, potassium cyclamate, erythritol, glycerol, lactitol, maltitol, mannitol, sorbitol, xylitol, galactitol, and combinations thereof.

3. The consumer product according to claim 1, wherein the high intensity sweetener is derived from *Stevia rebaudiana*, wherein the high intensity sweetener is selected from the group consisting of whole leaf and crude *stevia* extracts, modified *stevia* extracts, mono-, di- and polyglycosylated steviol compounds, green *stevia* powder, Rebaudioside A (Reb A), Rebaudioside B, Rebaudioside C, Rebaudioside D, Rebaudioside D2, Rebaudioside E, and Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Rebaudioside R, Rebaudioside S, Rebaudioside V, Rebaudioside W, Rebaudioside X, Rebaudioside KA, Dulcoside A, Rubusoside, stevioside, and other modified stevioglycosides, and combinations thereof.

4. The consumer product according to claim 1, wherein the high intensity sweetener is derived from *Siraitia grosvenorii*, wherein the high intensity sweetener is selected from the group consisting of modified or unmodified extracts, mogrosides, and combinations thereof.

5. The consumer product according to claim 1, wherein the high intensity sweetener is selected from the group consisting of methyl L-α-aspartyl-L-phenylalaninate, *Siraitia grosvenorii* extract, Rebaudioside A; and combinations thereof.

6. A method to modulate taste properties of a consumer product comprising a high intensity sweetener, wherein (4Z,7Z)-decadienal is added to the consumer product in an amount effective to modulate the taste profile of a high intensity sweetener, wherein (4Z,7Z)-decadienal is in an amount of from about 0.0001 ppt to about 1% by weight.

7. The method of claim 6, wherein (4Z,7Z)-decadienal is added to the consumer product in an amount of less than 0.1 ppm by weight.

8. The method of claim 6, wherein (4Z,7Z)-decadienal is added to the consumer product in an amount of from 0.10 ppt to less than 0.1 ppm.

9. The method of claim 6, wherein the consumer product is selected form the group consisting of a food product, a beverage product, an oral care product, a pharmaceutical, a pet food product, and an animal feed product.

10. The method of claim 6, wherein the high intensity sweetener is selected from the group consisting of 1,2-benzothiazol-3(2H)-one 1,1-dioxide (saccharin) or its sodium salt; methyl L-α-aspartyl-L-phenylalaninate (aspartame); acesulfame potassium (Ace-K or acesulfame K); 1,6-dichloro-1,6-dideoxy-β-D-fructofuranosyl-4-chloro-4-deoxy-α-D-alactopyranosideneotame (sucralose); (3S)-3-[3-(3-Hydroxy-4-methoxyphenyl)propylamino]-4-[[(2S)-1-methoxy-1-oxo-3-phenylpropan-2-yl]amino]-4-oxobutanoic acid (advantame); (3S)-3-(3,3-Dimethylbutylamino)-4-[[(2S)-1-methoxy-1-oxo-3-phenylpropan-2-yl]amino]-4-oxobutanoic acid (neotame), L-α-aspartyl-N-(2,2,4,4-tetramethyl-3-thietanyl)-D-alaninamide (alitame); sodium N-cyclohexylsulfamate, calcium cyclamate, sodium cyclamate, magnesium cyclamate, potassium cyclamate, erythritol, glycerol, lactitol, maltitol, mannitol, sorbitol, xylitol, galactitol and combinations thereof.

11. The method of claim 6, wherein the high intensity sweetener is derived from *Stevia rebaudiana*, wherein the high intensity sweetener is selected from the group consisting of whole leaf and crude *stevia* extracts, modified *stevia* extracts, mono-, di- and polyglycosylated steviol compounds, green *stevia* powder, Rebaudioside A (Reb A), Rebaudioside B, Rebaudioside C, Rebaudioside D, Rebaudioside D2, Rebaudioside E, and Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Rebaudioside R, Rebaudioside S, Rebaudioside V, Rebaudioside W, Rebaudioside X, Rebaudioside KA, Dulcoside A, Rubusoside, stevioside, and combinations thereof.

12. The method of claim 6, wherein the high intensity sweetener is derived from *Siraitia grosvenorii*, wherein the high intensity sweetener is selected from the group consisting of modified or unmodified extracts, mogrosides, and combinations thereof.

13. The method of claim 6, wherein the high intensity sweetener is selected from the group consisting of methyl L-α-aspartyl-L-phenylalaninate, *Siraitia grosvenorii* extract, Rebaudioside A, and combinations thereof.

14. The method of claim 6, wherein (4Z,7Z)-decadienal is added to the consumer product in an amount of from 0.0001 ppt to less than 0.1 ppm by weight.

15. The method of claim 1, wherein (4Z,7Z)-decadienal is added to the consumer product in an amount of less than 0.1 ppm by weight.

16. The method of claim 1, wherein (4Z,7Z)-decadienal is added to the consumer product in an amount of from 0.10 ppt to less than 0.1 ppm.

17. The method of claim 1, wherein (4Z,7Z)-decadienal is added to the consumer product in an amount of from 0.0001 ppt to less than 0.1 ppm by weight.

* * * * *